(12) United States Patent
Mito

(10) Patent No.: US 6,372,691 B2
(45) Date of Patent: Apr. 16, 2002

(54) METHOD FOR CONTROLLING WEEDS

(75) Inventor: Nobuaki Mito, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/735,611

(22) Filed: Dec. 14, 2000

(30) Foreign Application Priority Data

Dec. 16, 1999 (JP) ............................................. 11-357337

(51) Int. Cl.[7] ........................ A01N 43/54; C07D 239/553
(52) U.S. Cl. ........................ 504/243; 504/243; 544/312; 544/313; 544/314; 544/309; 544/310; 544/311
(58) Field of Search ........................... 504/243; 544/312, 544/314, 310, 309, 311

(56) References Cited

U.S. PATENT DOCUMENTS

| | | | | |
|---|---|---|---|---|
| 4,859,229 A | * | 8/1989 | Wenger et al. ................... | 71/92 |
| 5,084,084 A | * | 1/1992 | Satow et al. ..................... | 71/92 |
| 5,602,077 A | * | 2/1997 | Amuti et al. ................... | 504/243 |
| 6,074,989 A | * | 6/2000 | Andree et al. ................... | 504/243 |
| 6,107,252 A | * | 8/2000 | Andree et al. ................... | 504/243 |
| 6,251,828 B1 | * | 6/2001 | Andree et al. ................... | 504/243 |
| 6,277,789 B1 | * | 8/2001 | Andree et al. ................... | 504/243 |

FOREIGN PATENT DOCUMENTS

JP           9188676 A    *   7/1997

* cited by examiner

*Primary Examiner*—Sabiha Qazi
(74) *Attorney, Agent, or Firm*—Birch, Stewart, Kolasch & Birch, LLP

(57) ABSTRACT

The present invention relates to a method for controlling weeds in corn field which comprises applying a herbicidal composition comprising 2-[2-chloro-4-fluoro-5-{3-methyl-2,6-dioxo-4-(trifluoromethyl)-1,2,3,6-tetrahydropyrimidin-1-yl}phenoxy]propionic acid ester as an active ingredient to corn fields after seeding corn.

According to the present method, kinds of weeds in corn fields can be controlled widely and no problematic phytotoxicity to corn is caused.

5 Claims, No Drawings

METHOD FOR CONTROLLING WEEDS

This application claims priority of JP 11-357337 filed on Dec. 16, 1999.

FIELD OF THE INVENTION

The present invention relates to a method for controlling weeds in corn fields.

BACKGROUND ARTS

Many herbicidal composition have been commercially available, and used for controlling weeds in corn fields. There are, however, many species of weeds to be controlled and their growth extends over a long time. For this reason, requested are herbicides with higher herbicidal activity, wide herbicidal spectrum, and safety to corns.

DISCLOSURE OF THE INVENTION

The present inventor has intensively studied under such a circumstance. As a result, he has found that various weeds growing in corn fields can be controlled and no problematic phytotoxicity can be caused by applying a composition comprising 2-[2-chloro-4-fluoro-5-{3-methyl-2,6-dioxo-4-(trifluoromethyl)-1,2,3,6-tetrahydropyrimidin-1-yl}phenoxy]propionic acid ester as an active ingredient to corn fields after seeding corns, and he has accomplished the present invention.

Therefore, the present invention provides a method for controlling weeds in corn fields by applying a composition comprising 2-[2-chloro-4-fluoro-5-{3-methyl-2,6-dioxo-4-(trifluoromethyl)-1,2,3,6-tetrahydropyrimidin-1-yl}phenoxy]propionic acid ester (hereinafter, referred to as the present compound) as an active ingredient (referred to as the present herbicidal composition) to corn fields after seeding corns (hereinafter, referred to as the present method).

In the present compound, "ester" represents C1–C7 alkyl ester, C5–C6 cycloalkyl ester or C3–C6 alkenyl ester.

The production example of the present compound is shown below.

PRODUCTION EXAMPLE 1

In 70 ml of N,N-dimethylformamide, 6.7 g of 3-(4-chloro-2-fluoro-5-hydroxyphenyl)-1-methyl-6-trifluoromethyl-2,4-(1H,3H)-pyrimidindione (produced according to a method described in U.S. Pat. No. 4,859,229) was dissolved, and 4.2 g of potassium carbonate and 3.3 ml of methyl 2-chloropropionate were added thereto. The mixture was stirred at room temperature for 1 hour and at 100° C. for 45 minutes. After that, the reaction mixture was added into water and extracted with ethyl acetate. The organic layer was washed with saturated saline, dried over anhydrous magnesium sulfate and then, concentrated. The residue was subjected to silica gel column chromatography (eluent, hexane/ethylacetate=3/1) to give 5.82 g of methyl 2-[2-chloro-4-fluoro-5-{3-methyl-2,6-dioxo-4-(trifluoromethyl)-1,2,3,6-tetrahydropyrimidin-1-yl}phenoxy]propionate (hereinafter, referred to as Compound A).

Each of objective present compounds can obtained by conducting the same method as described in the above production example except that the reaction reagents described in the following table 1 are used in replace of methyl 2-chloropropionate.

TABLE 1

| Reaction reagent | Ester produced | Compound symbol |
| --- | --- | --- |
| Propyl 2-bromopropionate | propyl ester | B |
| Butyl 2-bromopropionate | butyl ester | C |
| Pentyl 2-chloropropionate | pentyl ester | D |
| Hexyl 2-bromopropionate | hexyl ester | E |
| Heptyl 2-bromopropionate | heptyl ester | F |
| i-Propyl 2-bromopropionate | i-propyl ester | G |
| i-Butyl 2-bromopropionate | i-butyl ester | H |
| t-Butyl 2-bromopropionate | t-butyl ester | I |
| c-Pentyl 2-bromopropionate | c-pentyl ester | J |
| c-Hexyl 2-bromopropionate | c-hexyl ester | K |
| Allyl 2-bromopropionate | allyl ester | L |
| Ethyl 2-bromopropionate | ethyl ester | M |

In the table, "i-", "t-", and "c-" represent iso-, tertiary-, and cyclo-, respectively.

Physical properties of some of the present compounds are shown below.

Compound A
$^1$H-NMR (CDCl$_3$, 300 MHz): δ (ppm) 7.31 (1H, d, J=9.0 Hz), 6.82 (1/2H, d, J=6.42 Hz), 6.81 (1/2H, d, J=6.45 Hz), 6.35 (1H, s), 4.68 (1H, q, J=6.9 Hz), 3.74 (3H, s), 3.55 (3H, s, br), 1.66 (3H, d, J=6.9 Hz)

Compound H
$^1$H-NMR (CDCl$_3$, 250 MHz): δ (ppm) 7.31 (1H, d, J=8.9 Hz), 6.82 (1/2H, d, J=6.5 Hz), 6.81 (1/2H, d, J=6.4 Hz), 6.34 (1H, s), 4.70 (1H, br, q, J=6.8 Hz), 3.98–3.85 (2H, m), 3.54 (3H, q, J=1.2 Hz), 1.90 (1H, m), 1.68 (3H, d, J=6.8 Hz), 0.862 (3H, d, J=6.7 Hz), 0.858 (3H, d, J=6.7 Hz)

Compound K
$^1$H-NMR (CDCl$_3$, 300 MHz): δ (ppm) 7.30 (1H, d, J=8.9 Hz), 6.82 (1/2H, d, J=6.5 Hz), 6.81 (1/2H, d, J=6.4 Hz), 6.33 (1H, d, J=1.5 Hz), 4.82 (1H, m), 4.66 (1H, q, J=6.7 Hz), 3.55–3.53 (3H, m), 1.90–1.30 (10H, m), 1.66 (3H, d, J=6.81 Hz)

Compound L
$^1$H-NMR (CDCl$_3$, 300 MHz): δ (ppm) 7.31 (1H, d, J=8.9 Hz), 6.84 (1/2H, d, J=6.50 Hz), 6.82 (1/2H, d, J=6.41 Hz), 6.34 (1H, s), 5.91–5.80 (1H, m), 5.29 (1H, ddd, J=1.1 Hz, 1.1 Hz, 17.1 Hz), 5.22 (1H, dd, J=1.1 Hz, 10.7 Hz), 4.71 (1H, q, J=7.1 Hz), 4.64 (2H, dd, J=1.1 Hz, 5.6 Hz), 3.55 (3H, t, J=1.45 Hz), 1.68 (3H, d, J=7.1 Hz)

According to the present method, the following kinds of weeds which cause problems in corn fields can be controlled.

Polygonaceae:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), Japanese knotweed (*Polygonum cuspidatum*)

Portulacaceae:
common purslane (*Portulaca oleracea*)

Caryophyllaceae:
common chickweed (*Stellaria media*)

Chenopodiaceae:
common lambsquarters (*Chenopodium album*), kochia (*Kochia scoparia*)

Amaranthaceae:
redroot pigweed (*Amaranthus retroflexus*), smooth pigweed (*Amaranthus hybridus*)

Cruciferae:
wild radish (*Raphanus raphanistrum*), wild mustard (*Sinapis arvensis*), shepherdspurse (*Capsella bursapastorsis*)

Leguminosae:
  hemp sesbania (*Sesbania exaltata*), sicklepod (*Cassia obtusifolia*), Florida beggarweed (*Desmodium tortuosum*), white clover (*Trifolium repens*)
Malvaceae:
  velvet leaf (*Abutilon theophrasti*), prickly sida (*Sida spinosa*)
Violaceae:
  field pansy (*Viola arvensis*), wild pansy (*Viola tricolor*)
Rubiaceae:
  catchweed bedstraw (cleavers) (*Galium aparine*)
Convolvulaceae:
  ivyleaf morningglory (*Ipomoea hederacea*), tall morningglory (*Ipomoea purpurea*), entireleaf morningglory (*Ipomoea hederacea var intergriuscula*), pitted morningglory (*Ipomoea lacunosa*), field bindweed (*Convolvulus arvensis*)
Labiatae:
  purple deadnettle (*Lamium purpureum*), henbit (*Lamium amplexicaule*)
Solanaceae:
  jimsonweed (*Datura stramonium*), black nightshade (*Solanum nigrum*)
Scrophulariaceae:
  persian speedwell (*Veronica persica*), ivyleaf speedwell (*Veronica hederaefolia*)
Compositae:
  common cocklebur (*Xanthium strumarium*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), japanese mugwort (*Artemisia princeps*), tall goldenrod (*Solidago altissima*)
Boraginaceae:
  field forget-me-not (*Myosotis arvensis*)
Asclepiadaceae:
  common milkweed (*Ascleplas syriaca*)
Euphorbiaceae:
  sun spurge (*Euphorbia helioscopia*), spotted spurge (*Euphorbia maculata*)
Gramineae:
  barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)
Commelinaceae:
  common dayflower (*Commelina communis*)
Equisetaceae:
  field horsetail (*Equisetum arvense*)
Cyperaceae:
  rice flatsedge (*Cyperus iria*), purple nutsedge (*Cyperus rotundus*), yellow nutsedge (*Cyperus esculentus*)

The present herbicidal composition can be usually formulated by mixing each of the present compounds with solid or liquid carriers or diluents, if necessary, surfactants, and/or other formulation auxiliary agents to become emulsifiable concentrates, wettable powders, flowables, and granules, and used.

These formulations may contain any of the present compounds as an active ingredient at an amount of 0.5% to 90% by weight, preferably 1% to 80% by weight, based on the total weight of the formulation.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfuric acid esters; alkylsulfonic acid salts; alkylarylsulfonic acid salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methoxyphenol), vegetable oils, mineral oils, fatty acids, and fatty acid esters.

The present herbicidal composition may be applied to weeds as such, or after diluted with water or the like. The present herbicidal composition may also be used in admixture with other herbicides, in which case the herbicidal activity can be expected to be enhanced. The present herbicidal composition can also be used together with insecticides, bactericides, fungicides, plant growth regulators, fertilizers, safener, soil conditioners, or other agents.

The application amount of the present compound, although it may vary with formulation types, application times, application places, and weeds to be controlled, is usually in the range of 1 to 200 g, more preferably 2 to 100 g, further preferably 5 to 80 g per hectare The present composition can be applied in corn fields after seeding corns, preferably at 2 leaf stage of corn or later.

Hereinafter, formulation examples are explained. In the examples, "part(s)" represents "part(s) by weight".

Formulation Example 1

Eighty (80) parts of compound A, compound B, compound C, compound D, compound E, compound F, compound G, compound H, compound I, compound J, compound K, compound L or compound M, 3 parts of calcium ligninsulfonate, 2 parts of sodium laurylsulfate, and 15 parts of synthetic hydrated silicon dioxide are well pulverized and mixed, to obtain wettable powders.

Formulation Example 2

Fifty (50) parts of compound A, compound B, compound C, compound D, compound E, compound F, compound G, compound H, compound I, compound J, compound K, compound L or compound M, 3 parts of polyoxyethylene sorbitan monooleate, 3 parts of CMC (carboxymethylcellulose), and 44 parts of water are mixed and wet pulverized until the particle size comes to 5 microns or smaller to give flowables.

Formulation Example 3

Ten (10) parts of compound A, compound B, compound C, compound D, compound E, compound F, compound G, compound H, compound I, compound J, compound K, compound L or compound M, 3 parts of polyoxyethylene sorbitan monooleate, 3 parts of CMC (carboxymethylcellulose), and 84 parts of water are mixed and wet pulverized until the particle size comes to 5 microns or smaller to give flowables.

Formulation Example 4

Fifty (50) parts of compound A, compound B, compound C, compound D, compound E, compound F, compound G, compound H, compound I, compound J, compound K, compound L or compound M, 3 parts of calcium ligninsulfonate, 2 parts of sodium laurylsulfate, and 45 parts of synthetic hydrated silicon dioxide are well pulverized and mixed, to obtain wettable powders.

Formulation Example 5

Ten (10) parts of compound A, compound B, compound C, compound D, compound E, compound F, compound G, compound H, compound I, compound J, compound K, compound L or compound M, 3 parts of calcium ligninsulfonate, 2 parts of sodium laurylsulfate, and 85 parts of synthetic hydrated silicon dioxide are well pulverized and mixed, to obtain wettable powders.

Next, test examples are explained.

The herbicidal activity was evaluated at 11 levels with indices of 0 to 10, i.e., designated by the numeral "0", "1", "2", "3", "4", "5", "6", "7", "8", "9" or "10" wherein "0" means that there was no or little difference in the degree of germination or growth between the treated and the untreated tested plants at the time of examination, and "10" means that the test plants died completely or their germination or growth was completely inhibited. The evaluation of phytotoxicity is as follows:

No harm: Phytotoxicity is hardly seen.
Slight: Slight phytotoxicity which does not affect the growth of corn is seen.
Light: Light phytotoxicity and light growth inhibition of corn are seen.
Middle: Middle phytotoxicity and growth inhibition of corn are seen.
Serious: Serious phytotoxicity and serious growth inhibition of corn are seen.

Test Example 1

Plastic pots having a diameter of 11 cm and a depth of 8 cm were filled with upland soil, and seeded with common lambsquarters (*Chenopodium album*), ivyleaf morningglory (*Ipomoea hederacea*), velvetleaf (*Abutilon theophrasti*), and corn. The test plants were grown in a greenhouse for 7 days. After that, other corn was further seeded in each of the above pots and the test plants were grown in the greenhouse for further 19 days. Emulsifiable concentrate comprising compound A obtained by well mixing 5 parts of compound A, 6 parts of Sorpol 3005X (produced by Toho Chemical Industry, Co., Ltd.) and 89 parts of xylene was diluted with prescribed amount of water, and the dilution was applied over the test plants uniformly using a small sprayer. The leaf stage of the corns grown for 26 days and 19 days were 2-leaf stage and 1-leaf stage, respectively. After the application, the test plants were grown in the greenhouse for 10 days and then, herbicidal activity and phytotoxicity to corn were examined. The results are shown in Table 2.

TABLE 2

| Test compound | Dosage (g/ha) | Herbicidal activity | | | Phytotoxicity | |
|---|---|---|---|---|---|---|
| | | La | Mo | Ve | C1 | C2 |
| Compound A | 20 | 10 | 10 | 10 | Slight | No harm |
| | 10 | 10 | 10 | 10 | No harm | No harm |
| | 5 | 9 | 10 | 10 | No harm | No harm |

La: common lambsquarters, Mo: ivyleaf morningglory
Ve: velvetleaf
C1: corn at 1-leaf stage, C2: corn at 2-leaf stage

Test Example 2

Plastic pots having a diameter of 11 cm and a depth of 8 cm were filled with upland soil, and seeded with common cocklebur (*Xanthium strumarium*). The test plants were grown in a greenhouse for 5 days. After that, corn was further seeded in each of the above pots and the test plants were grown in the greenhouse for further 16 days. Emulsifiable concentrate comprising compound A or Comparative compound obtained by well mixing 5 parts of compound A or Comparative compound, 6 parts of Sorpol 3005X (produced by Toho Chemical Industry, Co., Ltd.) and 89 parts of xylene was diluted with prescribed amount of water, and the dilution was applied over the test plants uniformly using a small sprayer. The leaf stage of the corns grown for 16 days were 2-leaf stage. After the application, the test plants were grown in the greenhouse for 10 days and then, herbicidal activity and phytotoxicity to corn were examined. The results are shown in Table 3.

TABLE 3

| Test compound | Dosage (g/ha) | Herbicidal activity Cocklebur | Phytotoxicity corn |
|---|---|---|---|
| Compound A | 10 | 10 | No harm |
| | 5 | 10 | No harm |
| | 2.5 | 10 | No harm |
| Comparative compound | 10 | 10 | light |
| | 5 | 10 | Slight |
| | 2.5 | 8 | No harm |

Comparative compound (Compound No. B-1 disclosed in U.S. Pat. No. 5,084,084)

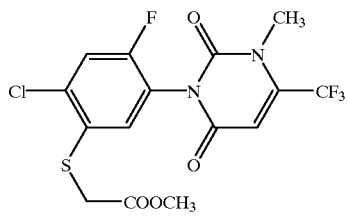

According to the present method, kinds of weeds in corn fields can be controlled widely and no problematic phytotoxicity to corn is caused.

What is claimed is:

1. A method for controlling weeds, which comprises applying an effective amount of a herbicidal composition comprising 2-[2-chloro-4-fluoro-5-{3-methyl-2,6-dioxo-4-(trifluoromethyl)-1,2,3,6-tetrahydropyrimidin-1-yl}phenoxy]propionic acid ester as an active ingredient to corn fields after seeding corn.

2. The method according to claim 1, wherein the herbicidal composition is applied at 2-leaf stage of corn or later.

3. The method according to claim 1 or 2, wherein the amount of 2-[2-chloro-4-fluoro-5-{3-methyl-2,6-dioxo-4-(trifluoromethyl)-1,2,3,6-tetrahydropyrimidin-1-yl}phenoxy]propionic acid ester is 1 to 200 g per hectare.

4. The method according to claim 1 to 2, wherein 2-[2-chloro-4-fluoro-5-{3-methyl-2,6-dioxo-4-(trifluoromethyl)-1,2,3,6-tetrahydropyrimidin-1-yl}phenoxy]propionic acid ester is methyl 2-[2-chloro-4-fluoro-5-{3-methyl-2,6-dioxo-4-(trifluoromethyl)-1,2,3,6-tetrahydropyrimidin-1-yl}phenoxy]propionate.

5. The method according to claim 1, wherein the ester is C1–C7 alkyl ester, C5–C6 cycloalkyl ester or C3–C6 alkenyl ester.

* * * * *